(12) United States Patent
Sibbitt

(10) Patent No.: US 6,962,576 B2
(45) Date of Patent: Nov. 8, 2005

(54) RECIPROCATING SYRINGES

(75) Inventor: Wilmer L. Sibbitt, Albuquerque, NM (US)

(73) Assignee: Science & Technology Corporation @ UNM, Albuquerque, NM (US)

( * ) Notice: Subject to any disclaimer, the term of this patent is extended or adjusted under 35 U.S.C. 154(b) by 824 days.

(21) Appl. No.: 09/795,010

(22) Filed: Feb. 28, 2001

(65) Prior Publication Data

US 2001/0009989 A1 Jul. 26, 2001

Related U.S. Application Data

(62) Division of application No. 09/303,555, filed on May 3, 1999, now Pat. No. 6,245,046.

(51) Int. Cl.$^7$ ................................................. A61M 5/00
(52) U.S. Cl. ..................................................... 604/191
(58) Field of Search ............................... 604/152, 191, 604/80, 81, 35, 181, 183, 187

(56) References Cited

U.S. PATENT DOCUMENTS

| | | | |
|---|---|---|---|
| 3,990,446 A | | 11/1976 | Taylor |
| 4,333,458 A | | 6/1982 | Margulies et al. |
| 4,484,915 A | | 11/1984 | Tartaglia |
| 4,639,248 A | | 1/1987 | Schweblin |
| 4,650,461 A | * | 3/1987 | Woods ......................... 604/28 |
| 4,687,472 A | | 8/1987 | Gross |
| 4,689,042 A | * | 8/1987 | Sarnoff et al. ................. 604/89 |
| 4,740,203 A | * | 4/1988 | Hoskins et al. ............. 604/191 |
| 5,135,511 A | | 8/1992 | Houghton et al. |
| 5,290,259 A | | 3/1994 | Fischer |
| 5,328,459 A | * | 7/1994 | Laghi ........................... 604/35 |
| 5,492,535 A | * | 2/1996 | Reed et al. .................. 604/152 |
| 5,498,246 A | | 3/1996 | Deutchman et al. |
| 5,529,463 A | * | 6/1996 | Layer et al. ................. 417/403 |
| 5,582,595 A | | 12/1996 | Haber et al. |
| 5,860,949 A | * | 1/1999 | Chen ............................ 604/35 |
| 5,957,883 A | * | 9/1999 | Lin .............................. 604/36 |
| 5,976,102 A | * | 11/1999 | Epstein ........................ 604/35 |

* cited by examiner

Primary Examiner—Sharon Kennedy
(74) Attorney, Agent, or Firm—Dorsey & Whitney LLP

(57) ABSTRACT

The present invention provides a syringe device comprising: a first syringe comprising: a first syringe barrel including a first opening at a distal end thereof through which fluid may be forced or aspirated; and a first syringe plunger sliding within the first syringe barrel for forcing fluid through the first syringe barrel opening, the first syringe plunger including a stopper at a distal end thereof which sealingly and slidably engages the first syringe barrel; a reciprocating member which moves along a track parallel to the axial direction of the first syringe; and a reciprocating device connecting the first syringe plunger to the reciprocating member so that when one member of the group consisting of the first syringe plunger and the reciprocating member moves distally, the other member of the group is forced to move proximally. The present invention also provides a syringe device where one member of the group consisting of the first syringe plunger and the reciprocating member moves proximally, the other member of the group is forced to move distally.

14 Claims, 10 Drawing Sheets

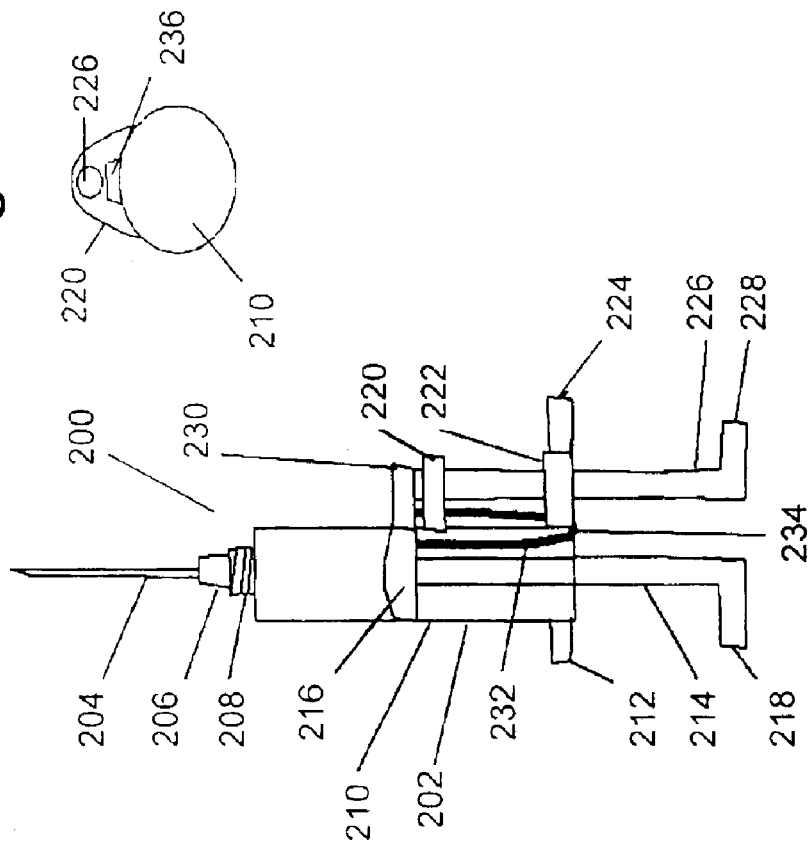
Fig. 2A
Fig. 2B
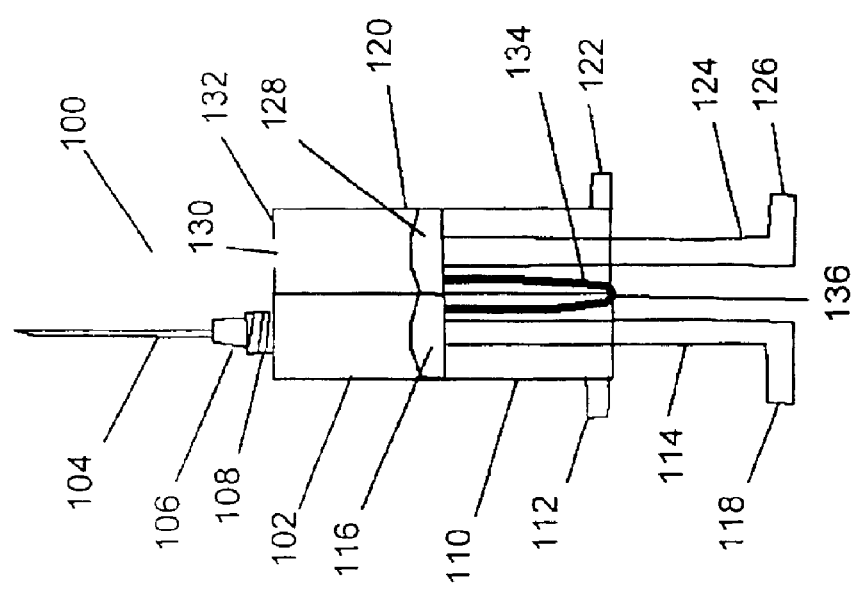
Fig. 1

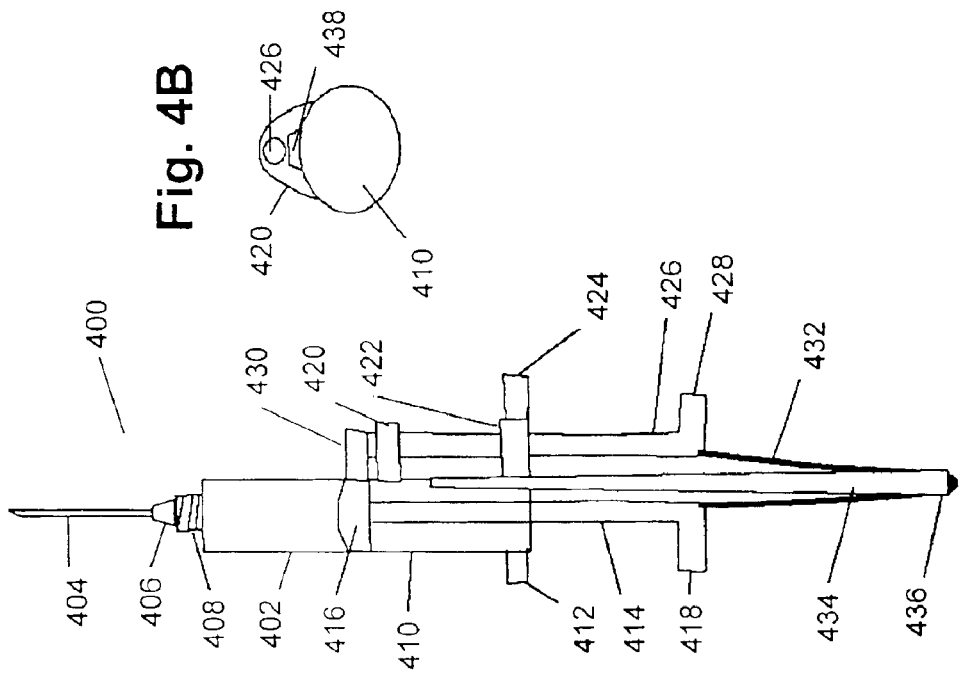
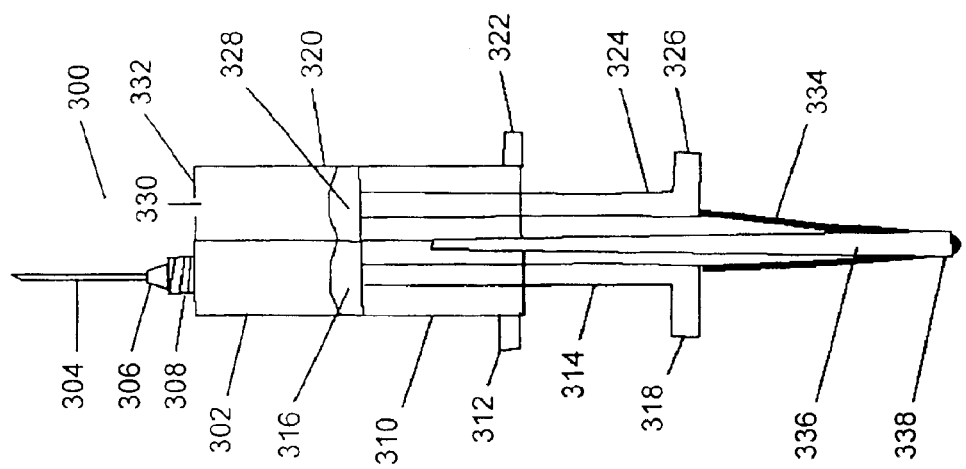

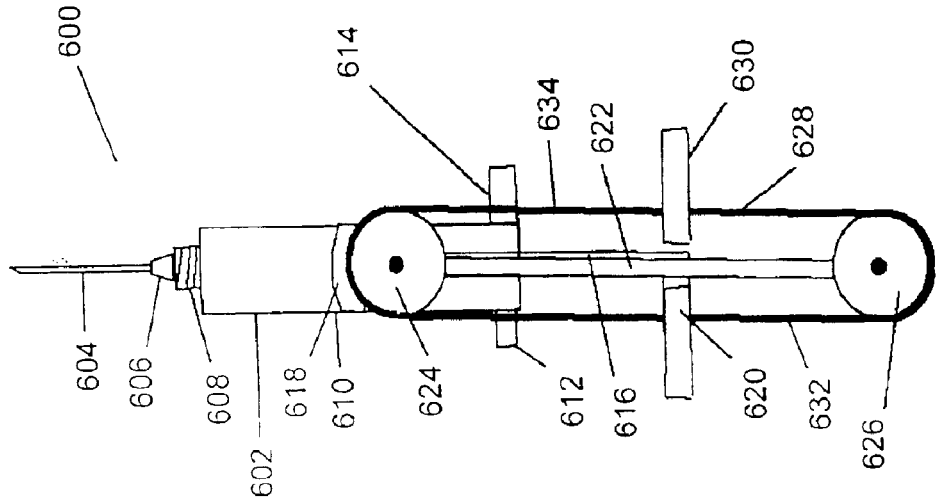
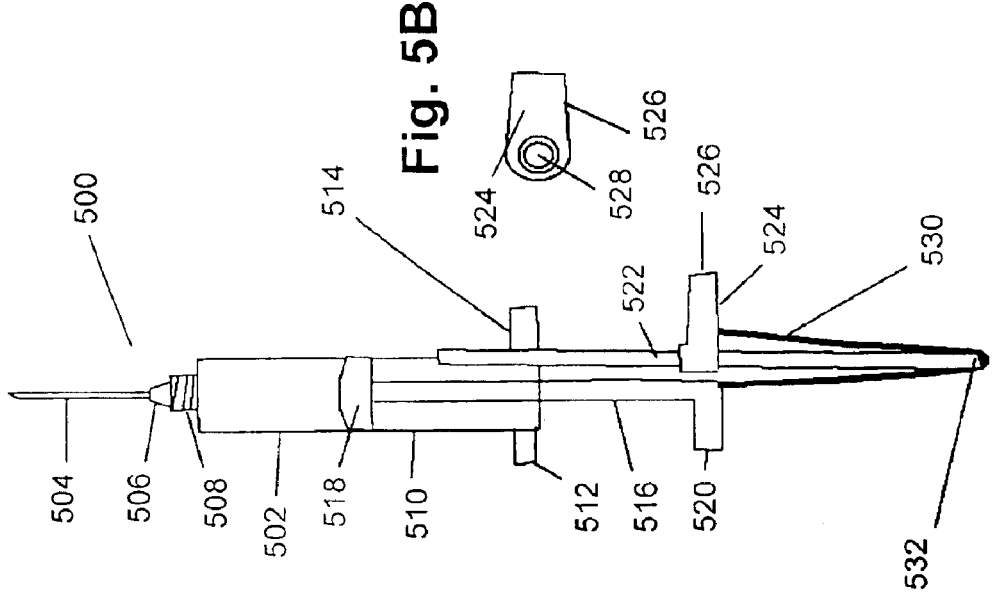

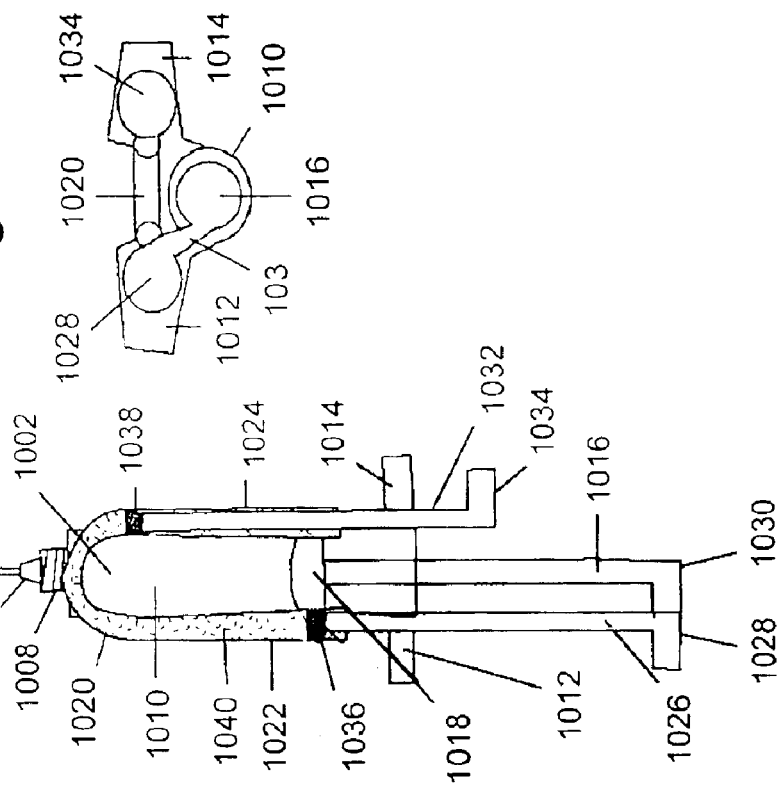
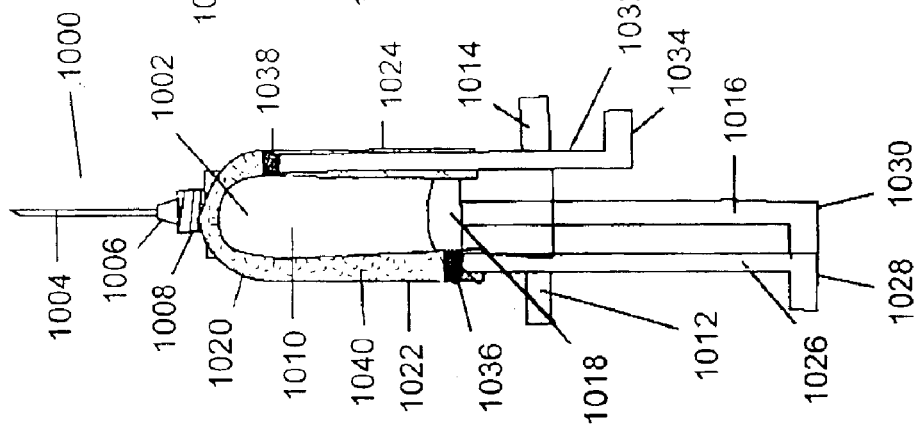
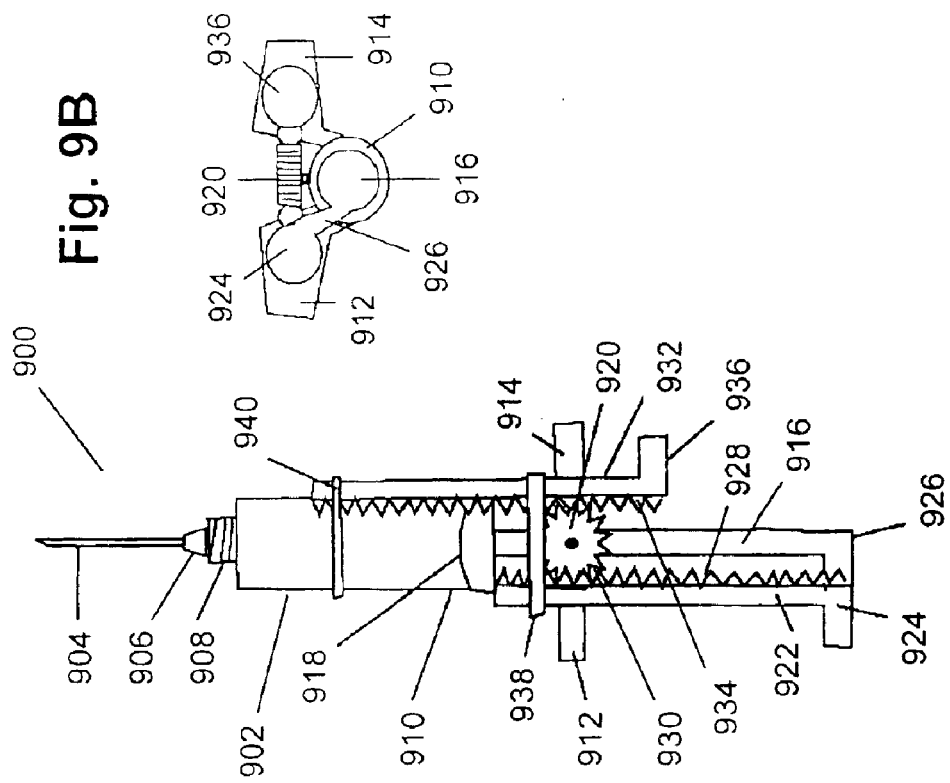

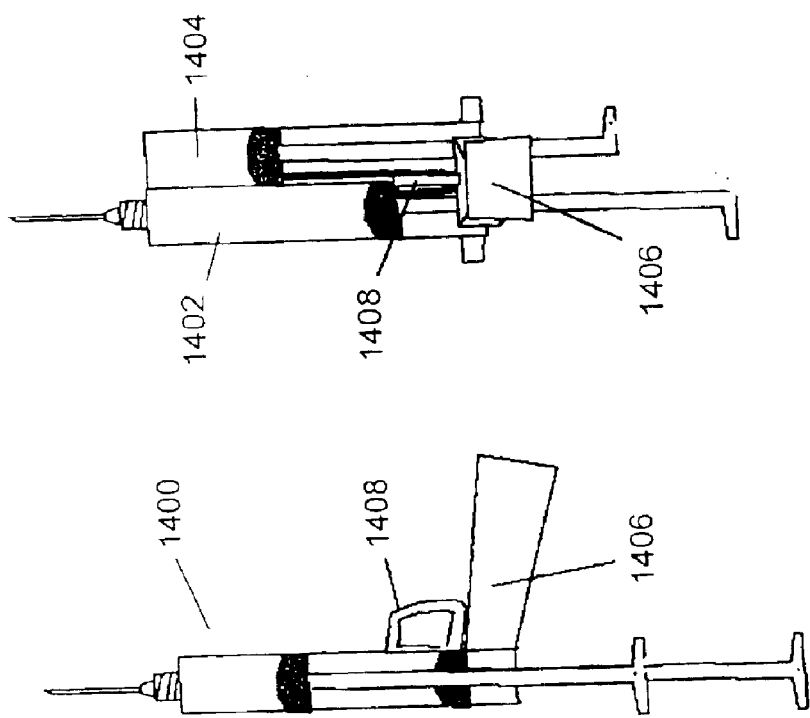
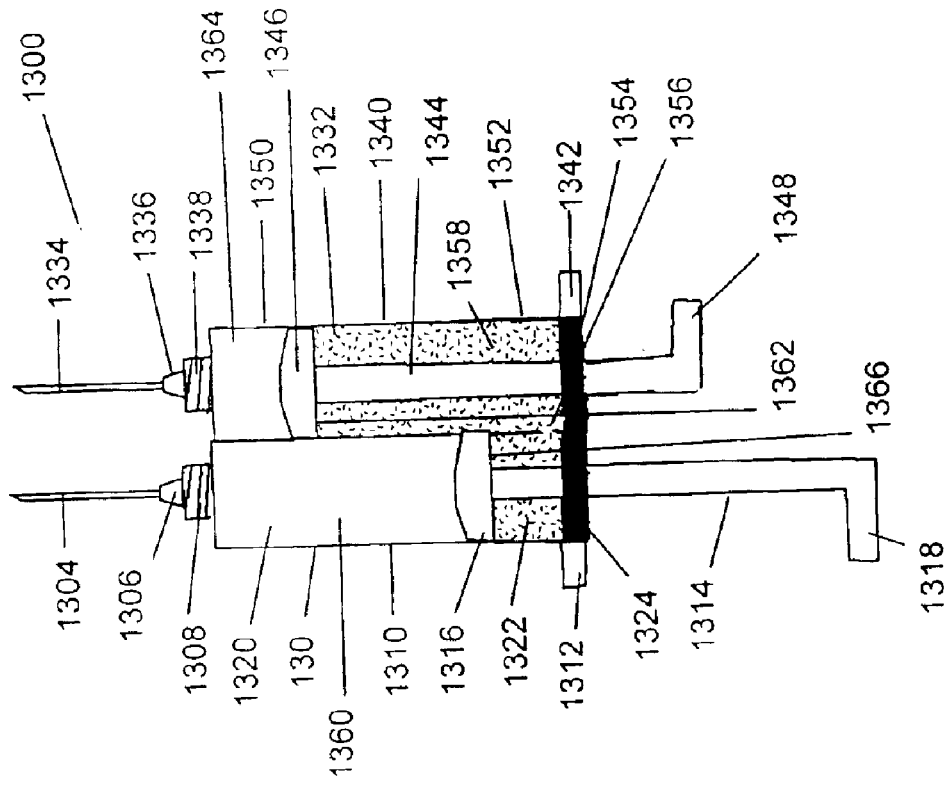

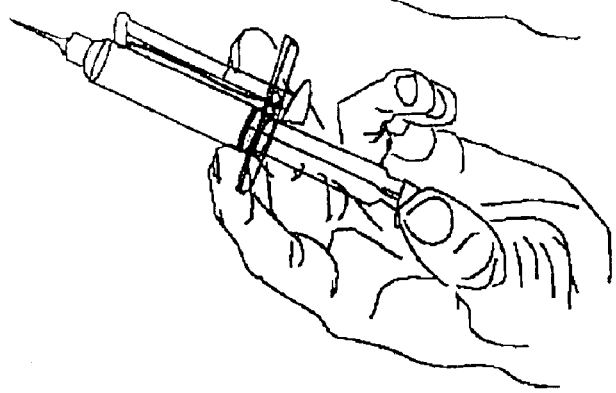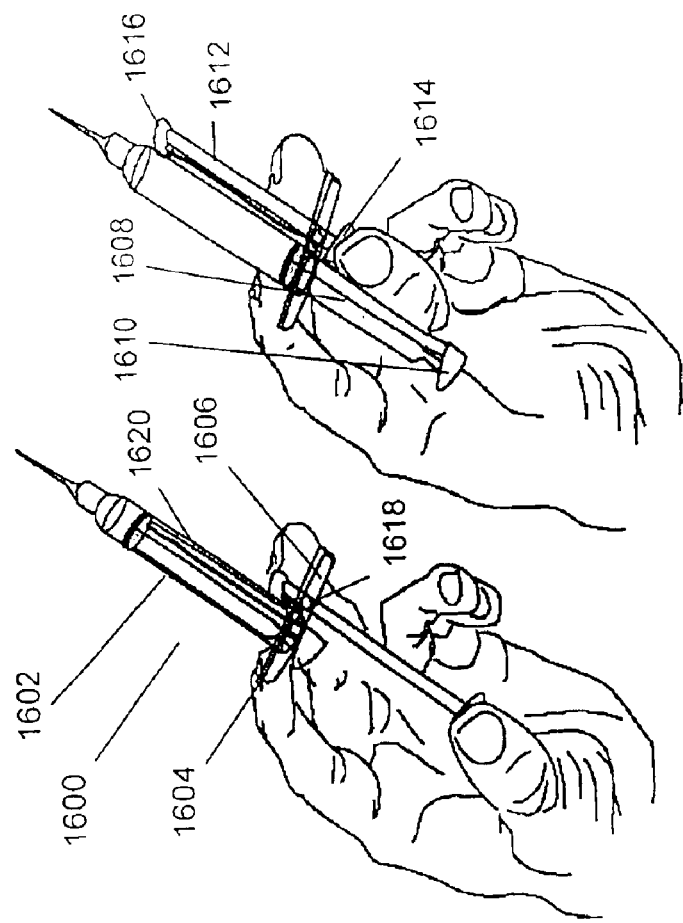

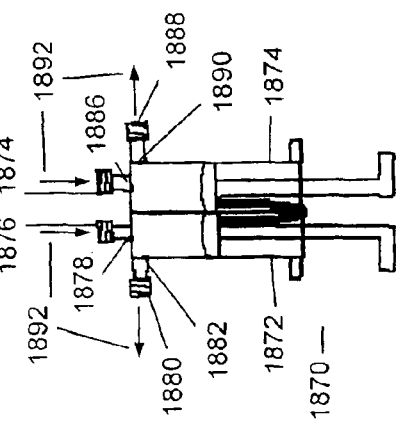
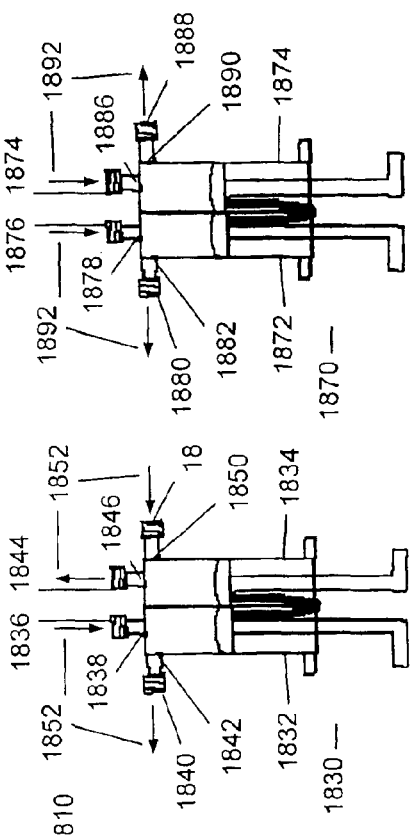
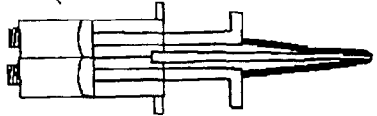
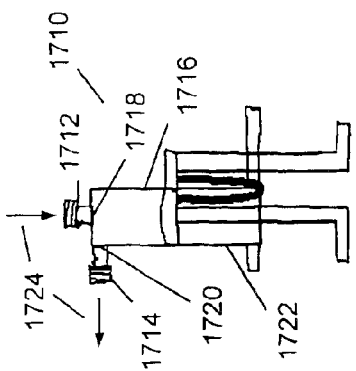
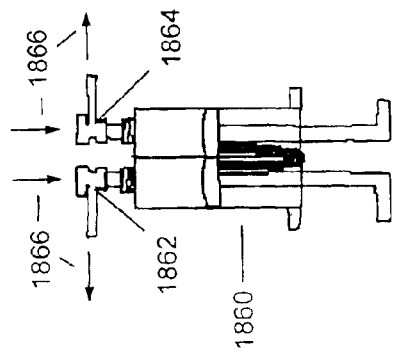
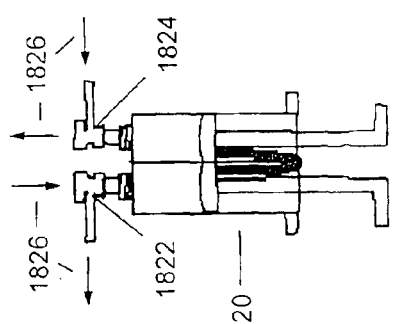
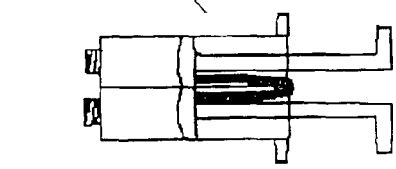
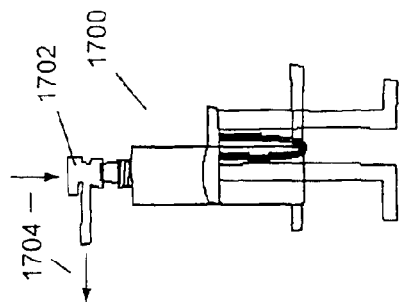

RECIPROCATING SYRINGES

CROSS-REFERENCE TO RELATED APPLICATION

The present application is a divisional of and claims the priority of U.S. patent application Ser. No. 09/303,555, entitled "Reciprocating Syringes" filed May 3, 1999, now U.S. Pat. No. 6,245,046. The entire disclosure and contents of the above mentioned application is hereby incorporated by reference.

BACKGROUND OF THE INVENTION

1. Field of the Invention

The present invention relates generally to single-handed syringe.

2. Description of the Prior Art

Syringes are an essential element in the day-to-day practice of medicine and nursing, but are also essential in industry, laboratory science, research, and animal husbandry. Syringes are used to inject medications, aspirate body fluids, provide vacuum, and transfer fluids. The syringe design most commonly used in medicine consists of a barrel made of plastic and an internal plunger which is moved into or out of the barrel, resulting in pressure or a vacuum, respectively. The difference in pressure between the volume in the syringe and the outside environment is produced by movement of the plunger, resulting in movement of fluid into (aspiration) or out (injection) of the syringe. This difference in pressure creates the desired effect of a syringe, that is, aspiration or injection.

Injection with a standard syringe is simple, and uses powerful flexor muscles of the hand and forearm. Injection with a standard syringe can usually be easily accomplished with one hand, freeing up the other hand for other necessary tasks or procedures. In this technique the 2nd (index) and 3rd fingers (middle finger) are placed on a finger flange of the syringe and the thumb is placed on a thumb rest of the plunger. The digits are brought together resulting in a powerful injection due to contraction of powerful flexor muscles of the hand and forearm. The ability to use a syringe with one hand and use the other hand for other tasks is important in many complicated procedures.

Aspiration with a standard syringe usually requires the use of two hands in order to generate the necessary power and maintain fine control. Generally, this is done by using one hand to control the barrel and the other hand to pull on the thumb rest of the plunger. The two-handed technique uses muscular strength of both the hands and the arm. Thus, very powerful vacuums with rapid movement of fluid into the syringe can be obtained. This is currently the technique of choice when either fine control of the syringe is required or considerable power is necessary. This is also the technique used by most physicians and nurses.

Single-handed aspiration with a standard syringe is possible, but is difficult and awkward. Generally, two techniques may be used. In the first method, the thumb rest of the plunger is grasped by the 2nd and 3rd digits (index finger and middle finger) and the thumb is placed on the finger flange of the syringe. The fingers are forcefully flexed, while the thumb remains extended. This results in the plunger being pulled out, resulting in an effective aspiration. There are several problems with this method including: 1) fine control of the syringe is effectively lost (which is important when there is a sharp needle in delicate living tissues); 2) the entire syringe tends to rotate, further degrading control; 3) due to the size of the syringe components relative to the dimensions and strength of the human hand this method is extremely difficult with syringes larger than 10 cc (i.e. 20 cc or 60 cc); and 4) the force of aspiration is generated by weak intrinsic flexors of the hand, without using powerful flexors of the thumb and forearm, resulting in a weaker aspiration. Thus, this single-handed method is unsatisfactory.

Single-handed aspiration may also be accomplished by an alternative thumb method. In this method, the syringe barrel is grasped by the four fingers, and the thumb is placed under the thumb rest of the plunger. With the syringe firmly grasped by the digits the thumb is extended, resulting in aspiration. Unfortunately, variations of this method are best demonstrated by drug addicts who inject themselves with drugs. The alternative thumb method has several disadvantages: 1) although a degree of control is maintained, it is not the fine control of the fingers, but the more coarse control of the forearm musculature; 2) power of the aspiration is weak, because it is accomplished by the extensors of the thumb; 3) full aspiration is difficult to achieve without changing the handgrip; 4) the syringe is generally pointing toward an operator which is the opposite direction required in a medical procedure (except for a person injecting themselves with drugs); and 5) when the thumb is extended the hypothenar tissues are compressed under the syringe, resulting in an unpredictable deviation of the needle side of the syringe with some loss of control.

Single-handed aspiration with a standard syringe is difficult and awkward, resulting in loss of fine control and power during aspiration. With loss of control, there is a higher rate of procedure failure and contamination. With loss of power, speed of aspiration is impaired, especially for viscous fluids. Because of the loss of strength and control with single-handed aspiration, procedures that demand either fine control of the syringe during aspiration or the generation of a powerful vacuum, are difficult if not impossible to accomplish with a conventional single-handed syringe.

Various attempts have been made to design a syringe which will allow for easier single-handed aspiration. Several of these designs have involved the use of a an external apparatus which is integral with the syringe and allows the plunger to be advanced or retracted using squeezing motions of digits on one hand rather than pulling motion using two hands, see for example U.S. Pat. No. 3,990,446; to Taylor et al. Other patents, such as U.S. Pat. No. 5,582,295; to Haber et al., have described essentially the same device, and some patents have described an adapter which can be fitted on a conventional syringe, see U.S. Pat. No. 5,135,511; to Houghton.

Several U.S. patents have described a syringe with an external slide which attaches to the plunger, permitting single-handed operation, see U.S. Pat. No. 4,484,915; to Tartaglia and U.S. Pat. No. 4,639,248; to Schweblin.

However, in all of the above-described designs, the position of the index and middle fingers as well as the thumb, must be moved on the syringes when switching from aspiration to injection mode, resulting in intraoperative instability. In addition, during single-handed aspiration using these devices, the barrel and needle advance beyond the index and ring finger, an unstable situation, creating major difficulties in control and localization of the needle and resulting in instability and unpredictability during procedures.

SUMMARY OF THE INVENTION

It is, therefore, an object of the present invention to provide a syringe that permits both injection and aspiration with one hand, yet maintains fine motor control and the strength necessary to generate high pressures and vacuums.

It is another object of the present invention to provide a stable platform for both injection and aspiration with the index and middle fingers in a fixed position, with the only required movement being a lateral movement of the thumb to a reciprocating plunger.

A first aspect of the present invention provides a syringe device comprising: a first syringe barrel including a first opening at a distal end thereof through which fluid may be forced or aspirated; and a first syringe plunger sliding within the first syringe barrel for forcing fluid through the first syringe barrel opening, the first syringe plunger including a stopper at a distal end thereof which sealingly and slidably engages the first syringe barrel; a reciprocating member which moves along a track parallel to the axial direction of the first syringe; and a reciprocating device connecting the first syringe plunger to the reciprocating member so that when one member of the group consisting of the first syringe plunger and the reciprocating member moves distally, the other member of the group is forced to move proximally.

A second aspect of the present invention provides a syringe device comprising: a first syringe comprising: a first syringe barrel including an opening at a distal end thereof through which fluid may be forced or aspirated; and a first syringe plunger sliding within the first syringe barrel for forcing fluid through the first syringe barrel opening, the first syringe plunger including a stopper at a distal end thereof which sealingly and slidably engages the first syringe; a reciprocating member which moves along a track parallel to the axial direction of the first syringe; and a reciprocating device connecting the first syringe plunger to the reciprocating member so that when one member of the group consisting of the first syringe plunger and the reciprocating member moves proximally, the other member of the group is forced to move distally.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 1 is a schematic side view of a syringe device of the present invention;

FIG. 2A is a schematic side view of a syringe device of the present invention;

FIG. 2B is an axial cross-sectional view of a guide support of the syringe device of FIG. 2A;

FIGS. 3 and 4A are schematic side views of syringe devices of the present invention;

FIG. 4B is an axial cross-sectional view of a guide support of the syringe device of FIG. 4A;

FIG. 5A is a schematic side view of a syringe device of the present invention;

FIG. 5B is an axial cross-sectional view of a sliding thumb rest of the syringe device of FIG. 5A;

FIG. 6 is a schematic side view of a syringe device of the present invention;

FIG. 9A is a schematic side view of a syringe device of the present invention;

FIG. 9B is an axial cross-sectional schematic view of the syringe device of FIG. 9A;

FIG. 10A is a schematic side view of a syringe device of the present invention;

FIG. 10B is an axial cross-sectional schematic view of the syringe device of FIG. 9A;

FIGS. 11, 12, 13, 14A, 14B, 15A, 15B, and 15C are schematic side views of syringe devices of the present invention;

FIGS. 16A, 16B, 16C, and 16D illustrate the use of a syringe device of the present invention;

FIG. 17A is a schematic side view of a syringe device of the present invention which has an external valve;

FIG. 17B is a schematic side view of a syringe device of the present invention which has an internal set of valves; and FIGS. 18A, 18B, 18C, 18D, 18E, and 18F are schematic side views of syringe devices of the present invention having two functional syringe barrels.

DETAILED DESCRIPTION OF THE PREFERRED EMBODIMENT

Definitions

Figure 8:
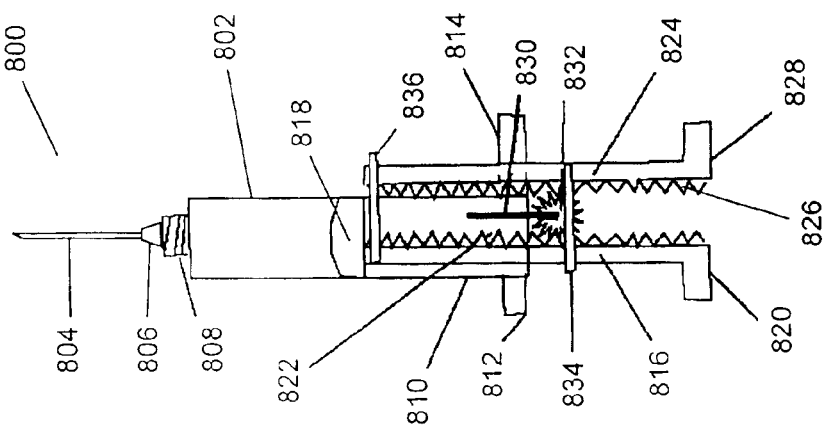
FIG. 8 is a schematic side view of a syringe device of the present invention.

For the purposes of the present invention, the term "axial direction of a syringe" refers to the line along a center axis of a syringe from its distal end to its proximal end or from its proximal end to its distal end.

For the purposes of the present invention, the term "proximal" refers to a direction towards a user of a syringe. For the purposes of the present invention, the term "distal" refers to a direction away from the user of the syringe.

For the purposes of the present invention, the term "reciprocating member" refers to plungers, sliders, thumb rest mounted on a belt, plunger with teeth on one side, etc., which is connected to a syringe plunger by a reciprocating device and moves in a direction opposite a direction of motion of the syringe plunger to which the reciprocating member is connected.

For the purposes of the present invention, a "reciprocating device" refers to a device which combines the functions of connecting a syringe plunger to a reciprocating member and causing the directions of motion of the syringe plunger and reciprocating member to be in opposite directions. Examples of a reciprocating device include: a connecting cord running over a round smooth edge of a syringe wall; a connecting cord which runs through a pulley mounted on a pulley post; a notched connecting cord running through a geared pulley, a gear mounted on a support and teeth mounted on a syringe plunger and reciprocating member which engages the gear; a U-tube filled with a liquid; etc.

For the purposes of the present invention, the term "track" refers to any means which constrains the motion of a reciprocating member such as a hollow syringe barrel in which a reciprocating member slides; a post on which a reciprocating member slides; a combination of retaining band, a gear mounted on a support, and teeth mounting on the reciprocating member which engages the gear, etc.

Description

Although two compartment and double plunger syringes have been described before in prior patents, these syringes have usually been based on a single barrel and are intended to mix or administer two different substances, see U.S. Pat. No. 3,685,514; to Cheney and U.S. Pat. No. 5,186,616; to Nadal. Other patents have also described double piston devices, either mechanically or hydraulically driven, for aspirating fluids or administering medications, see U.S. Pat. No. 4,036,232; to Genese and U.S. Pat. No. 4,437,859; to Whitehouse. However, none of these patents have described a device similar to the present invention that utilizes a reciprocating, thumb-operated, double-plunger syringe device intended for both aspiration and injection.

The present invention provides a syringe that permits injection and aspiration of fluids or gas using one hand with applications to health care, research, animal husbandry, and industry. The present invention utilizes fundamental changes in syringe design. In one embodiment, the syringe of the present invention includes an internal or external accessory plunger, with or without an accessory barrel, which is mechanically associated with the plunger of the functional syringe, resulting in a set of reciprocating plungers. Thus, when one plunger is depressed with the thumb, the syringe injects and when the accessory plunger is depressed with the same thumb, the syringe aspirates. This arrangement permits the index and middle fingers to stay in one position during aspiration and injection, while the thumb only need move laterally to the alternative plunger in order to change the direction of flow, i.e. aspiration or injection.

The resulting syringe is highly stable since only thumb position changes, and very powerful vacuums or pressures may be developed since powerful flexors of fingers, thumb, and forearm are used for both aspiration and injection. The syringe of the present invention is designed to be used with one hand, but may be used in all cases where standard syringes are used. This syringe may have particular uses in medical procedures when single-handed injection/aspiration is required, such as cardiac catheterization, emergency procedures, certain types of surgery, pediatric, and veterinary procedures, and in those handicapped individuals who can only use one hand. The applicability of these new syringe designs is expected to be large.

FIG. 1 illustrates a syringe device 100 of one preferred embodiment of the present invention. Syringe device 100 of FIG. 1 includes a modified conventional syringe 102 made of plastic, glass, or other material. On syringe 102 there is mounted a needle or cannula 104 having a hub 106. Hypodermic needle or cannula 104 is held on syringe 102 by a conventional needle or cannula fitting 108 such as a luer, Luer-Lok, etc. Syringe 102 includes a syringe barrel 110 with a finger flange 112. A syringe plunger 114, inserted into syringe barrel 110, includes a stopper 116, made from rubber or another flexible or tight-sealing material, and a thumb rest 118. Mounted on one side of syringe 102 is an accessory barrel 120 having a finger flange 122. Finger flange 122 is effectively joined to syringe barrel 110 by accessory barrel 120. Accessory barrel 120 provides a track for movement of a reciprocating accessory plunger 124 having a thumb rest 126 and a stopper 128 which may be similar or different from stopper 116. Barrels 110 and 120 maybe integrated together by bonding, retaining bands, simultaneous extrusion, casting, gluing, or any other method of integrating components. Accessory barrel 120 has an opening 130 at a distal end 132 to permit movement of gas in or out of accessory barrel 120. Barrel 120, unlike syringe barrel 110, is meant only to confine movement of accessory plunger 124 and not to transfer fluid or gas. There may be more than one opening for gas release and accessory barrel 120 may also include one or more openings on a side of the accessory barrel 120. Plungers 114 and 124 or stoppers 116 and 128 are mechanically attached by a connector 134 which may be a cord, line, string, wire, strap, band, chain, etc., which reaches from one plunger/stopper to the other by going over the sides of both barrels 110 and 120. In the embodiment shown in FIG. 1, stoppers 116 and 128 are connected by connector 134. Pulley structure 136, where the mechanical attachment as defined above contacts the junction of the two barrels functions as a pulley device which may take on a number of configurations as shown in other embodiments of the present invention, described below. In the embodiment shown in FIG. 1, pulley structure 136 is merely an edge of a wall that is preferably smooth and rounded to provide for easy sliding movement of connector 134. The above-described mechanical arrangement results in a reciprocating, thumb-operated, double-plunger syringe device that may be operated with one hand and effects both aspiration and injection.

Syringe barrel and accessory barrel of the embodiment of FIG. 1 need not be the same size. Also, accessory, barrel can be much smaller in diameter and have portions removed to save material and still function as a guide for the reciprocating accessory plunger. The above-described mechanical arrangement results in a reciprocating, thumb-operated, double-plunger syringe device that can be operated with one hand and effects both aspiration and injection. The accessory barrel may be external to the syringe barrel, as shown in FIG. 1, or internal to the syringe barrel (not shown).

FIGS. 2A and 2B illustrate a syringe device 200 of another preferred embodiment of the present invention. Syringe device 200 of FIGS. 2A and 2B includes a modified conventional syringe 202 made of plastic, glass, or other suitable material. On syringe 202 there is mounted a needle or cannula 204 having a hub 206. Hypodermic needle or cannula 204 is held on syringe 202 by a conventional needle or cannula fitting 208 such as a Luer, Luer-Lok, etc. Syringe 202 includes a syringe barrel 210 with a finger flange 212. A syringe plunger 214 inserted into syringe barrel 210 includes a stopper 216, made from rubber or another flexible or tight-sealing material, and a thumb rest 218. Conventional syringe 202 modified by addition of two guide supports 220 and 222. A finger flange 224 is mounted on upper guide support 222. Supports 220 and 222 provide a track for movement of a reciprocating accessory plunger 226 having a thumb rest 228. Guide supports 220 and 222 function similarly to the accessory barrel of the embodiment shown in FIG. 1. On a distal end of accessory plunger 226 there is a connector support 230 to which is connected a connector 232 and is also connected to syringe stopper 216. The connector may be a cord, line, string, wire, strap, band, chain, etc. which contacts pulley device 234 mounted on syringe barrel 210, creating a pulley FIG. 2B shows an opening 236 between guide supports 220 and syringe barrel 210 through which connector 232 may travel. A similar opening exists between upper guide support 222 and syringe barrel 210. The above-described mechanical arrangement results in a reciprocating, thumb-operated, double-plunger syringe device that may be operated with one hand and effects both aspiration and injection.

The guide supports of the embodiment of FIGS. 2A and 2B may be external to the syringe barrel, as shown in FIGS. 2A and 2B or located inside the syringe barrel (not shown).

FIG. 3 illustrates a syringe device 300 of another preferred embodiment of the present invention. Syringe device 300 of FIG. 3 includes a modified conventional syringe 302 made of plastic, glass, or other suitable material. On syringe 302 there is mounted a needle or cannula 304 having a hub 306. Hypodermic needle or cannula 304 is held on syringe 302 by a conventional needle or cannula fitting 308 such as a luer, Luer-Lok, etc. Syringe 302 includes a syringe barrel 310 with a finger flange 312. A syringe plunger 314 inserted into syringe barrel 310 and includes a stopper 316, made from rubber or another flexible or tight-sealing material, and a thumb rest 318. Mounted on one side of syringe 302 is an accessory barrel 320 having a finger flange 322. Finger flange 322 is effectively joined to syringe barrel 310 by accessory barrel 320. Accessory barrel 320 provides for the movement of a reciprocating accessory plunger 324 having a thumb rest 326 and a stopper 328 which may be similar or different from stopper 316. Barrels 310 and 320 may be integrated together by bonding, retaining bands, simultaneous extrusion, casting, gluing, or any other method of integrating components. Accessory barrel has an opening 330 at a distal end 332 to permit movement of gas in or out of accessory barrel 320. Barrel 320, unlike syringe barrel 310, is meant only to confine the movement of accessory plunger 324 and not to transfer fluid or gas. Syringe plunger thumb rest 318 and accessory plunger thumb rest 326 are mechanically connected by a connector 334, which may be a cord, line, string, wire, strap, band, chain, etc. A central pulley post 336 including extends proximally from where syringe barrel 310 and accessory barrel 320 join. Connector 332 extends over pulley post 336 and contacts pulley post 336 at a pulley device 338, which may have a number of configurations as described below. The above-described mechanical arrangement results in a reciprocating, thumb-operated, double-plunger syringe device that can be operated with one hand and effects both aspiration and injection.

The syringe barrel and accessory barrel need not be the same size. Also, the accessory barrel may be much smaller in diameter and have portions removed to save material and still function as a guide for the reciprocating accessory plunger. The accessory barrel may be external to the syringe barrel, as shown in FIG. 3, or internal to the syringe barrel (not shown).

FIGS. 4A and 4B illustrate a syringe device 400 of another preferred embodiment of the present invention. Syringe device 400 of FIGS. 4A and 4B includes a modified conventional syringe 402 made of plastic, glass, or other suitable material. On syringe 402 there is mounted a needle or cannula 404 having a hub 406. Hypodermic needle or cannula 404 is held on syringe 402 by a conventional needle or cannula fitting 408 such as a luer, Luer-Lok, etc. Syringe 402 includes a syringe barrel 410 with a finger flange 412. A syringe plunger 414 inserted into syringe barrel 410 includes a stopper 416, made from rubber or another flexible or tight-sealing material, and a thumb rest 418. Conventional syringe 402 modified by the addition of two guide supports 420 and 422. A finger flange 424 is mounted on upper guide support 422. Supports 420 and 422 provide a track for the movement of a reciprocating accessory plunger 426 having a thumb rest 428. Guide supports 420 and 422 function similarly to the guide supports of the embodiment shown in FIG. 2. On a distal end of accessory plunger 426 there is a sliding support 430 which slides along the outside of syringe barrel 410. A connector 432 connects thumb rests 418 and 428. Connector 432 may be a cord, line, string, wire, strap, band, chain, etc. A pulley post 434 extends proximally from where syringe barrel 410 and upper guide support 422 are joined. Connector 432 extends over pulley post 434 and contacts pulley post 434 at a pulley device 436, which can have a number of configurations as described below. FIG. 4B shows an opening 438 between guide supports 420 and syringe barrel 410 through which connector 432 may travel. A similar opening exists between upper guide support 422 and syringe barrel 410. The above-described mechanical arrangement results in a reciprocating, thumb-operated, double-plunger syringe device that may be operated with one hand and effects both aspiration and injection.

The guide supports of the embodiment of FIGS. 4A and 4B may be external to the syringe barrel, as shown in FIGS. 4A and 4B, or located inside the syringe barrel (not shown).

FIGS. 5A and 5B illustrate a syringe device 500 of another preferred embodiment of the present invention. Syringe device 500 of FIGS. 5A and 5B includes a modified conventional syringe 502 made of plastic, glass, or other suitable material. On syringe 502 there is mounted a needle or cannula 504 having a hub 506. Hypodermic needle or cannula 504 is held on syringe 502 by a conventional needle or cannula fitting 508 such as a Luer, Luer-Lok, etc. Syringe 502 includes a syringe barrel 510 with two finger flanges 512 and 514. A syringe plunger 516 inserted into syringe barrel 510 includes a stopper 518, made from rubber or another flexible or tight-sealing material, and a thumb rest 520. Adjacent to finger flange 514 is a pulley post 522 extending proximally from syringe 502. A slider 524 has a thumb rest 526 and opening 528, shown in FIG. 5B, which allows slider 524 to slide up and down pulley post 522. A connector 530 connects syringe thumb rest 520 and slider thumb rest 526. Connector 530 may be a cord, line, string, wire, strap, band, chain, etc. Connector 530 extends over pulley post 522 and contacts pulley post 522 at a pulley device 532, which may have a number of configurations as described below. The above-described mechanical arrangement results in a reciprocating, thumb-operated, double-plunger syringe device that may be operated with one hand and effects both aspiration and injection.

FIG. 6 illustrates a syringe device 600 of another preferred embodiment of the present invention. Syringe device 600 of FIG. 6 includes a modified conventional syringe 602 made of plastic, glass, or other suitable material. On syringe 602 there is mounted a needle or cannula 604 having a hub 606. Hypodermic needle or cannula 604 is held on syringe 602 by a conventional needle or cannula fitting 608 such as a luer, Luer-Lok, etc. Syringe 602 includes a syringe barrel 610 with two finger flanges 612 and 614. A syringe plunger 616 inserted into syringe barrel 610 includes a stopper 618, made from rubber or another flexible or tight-sealing material, and a thumb rest 620. Mounted on one side of syringe barrel 610 between two finger flanges 612 and 614 is a pulley post 622. Mounted on pulley post 622 are a distal pulley 624 and a proximal pulley 626. Thumb rest 620 includes a neck portion (not shown in FIG. 6) which extends thumb rest 620 out of the plane of syringe barrel 610, so that thumb rest 620 is in substantially the same plane as pulleys 624 and 626. A belt connector 628 travels over both pulleys 624 and 626. Syringe plunger thumb rest 620 and a reciprocating thumb rest 630 are both mechanically attached to belt connector 630 on parallel strands 632 and 634 of belt connector 630 by conventional means such as glue, interlocking notches on belt connector 630 and thumb rests 620 and 630, and other known means. Reciprocating thumb rest 630 is substantially in the same plane as the syringe plunger thumb rest 620 and pulleys 624 and 626. The engagement between the pulleys and the belt connector may take a number of forms as described below. The above-described mechanical arrangement results in a reciprocating, thumb-operated, double-plunger syringe device that may be operated with one hand and effects both aspiration and injection.

Figure 7A:
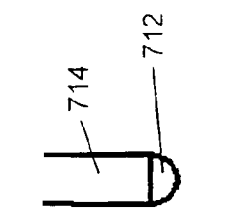
FIGS. 7A through 7F are schematic side views of pulley devices of the present invention.
Figure 7B:
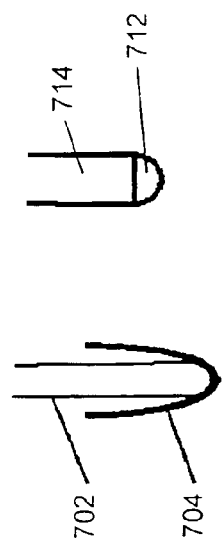
Figure 7C:
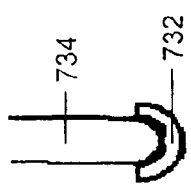
Figure 7D:
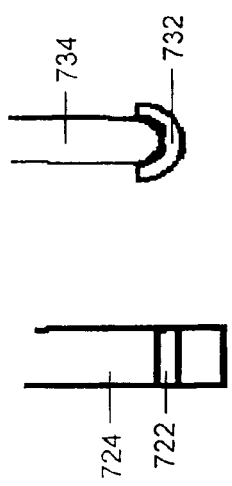
Figure 7E:
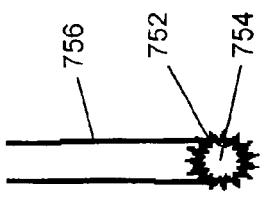
Figure 7F:
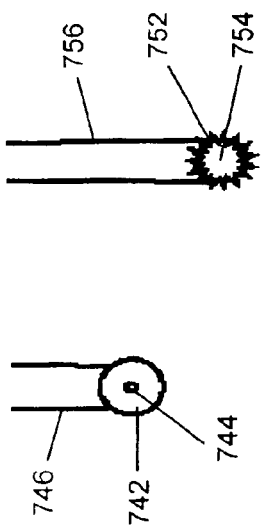

FIGS. 7A through 7F illustrate some of the configurations the pulley devices of the present invention may have. FIG. 7A illustrates a pulley device 702 of the present invention which is a round smooth edge of the side of a syringe barrel (not shown) or a pulley post (not shown) over which a connector 704 slides. FIG. 7B illustrates a pulley device 712 of the present invention which is a smooth or groove tip of plastic, metal or other low-friction material mounted on a flat surface of a support 714. FIG. 7C illustrates a pulley device 722 of the present invention which is a hole or grommet, drilled or inserted in a post 724. Hole or grommet may be made of plastic, metal, or other low-friction materials. Hole or grommet may either be straight (shown) or curved (not shown). FIG. 7D illustrates a pulley device 732 of the present invention which is a tip cover, grooved or curved-columnar and made of plastic, metal, or low friction material, mounted on a curved support 734. FIG. 7E illustrates a pulley device 742 of the present invention which is a rotating pulley with a central pin or axle 744 which engages a connector 746 that may be a cord, belt, chain, etc. FIG. 7F illustrates a pulley device 752 of the present invention which is a rotating gear pulley that rotates on a central pin or axle 754 and engages a connector 756 that may be chain, notched cord, etc.

FIG. 8 illustrates a syringe device 800 of another preferred embodiment of the present invention. Syringe device 800 of FIG. 8 includes a modified conventional syringe 802 made of plastic, glass, or other suitable material. On syringe 802 there is mounted a needle or cannula 804 having a hub 806. Hypodermic needle or cannula 804 is held on syringe 802 by a conventional needle or cannula fitting 808 such as a luer, Luer-Lok, etc syringe 802 includes a syringe barrel 810 with two finger flanges 812 and 814. A syringe plunger 816 inserted into syringe barrel 810 includes a stopper 818, made from rubber or another flexible or tight-sealing material, and a thumb rest 820. Syringe plunger includes teeth or notches 822 on one side. An reciprocating accessory plunger 824 is located on the outside of syringe barrel 810 and includes teeth or notches 826 on one side and a thumb rest 828 at the proximal end of accessory plunger 824. A gear pulley post 830 is mounted on and extends proximally from syringe barrel 810. Mounted on gear pulley post 830 is a gear pulley 832, which engages teeth 822 and 826 on syringe plunger 816 and accessory plunger 824, respectively. A proximal retaining band 834 is fixed to pulley post 830 or syringe barrel 810 and surrounds syringe plunger 816 and accessory plunger 824 permitting plungers 816 and 824 to move along defined tracks and keeping teeth 822 and 826 of plungers 816 and 824, respectively in contact with gear pulley 832. A distal retaining band 836 is fixed to accessory plunger 824 and surrounds syringe barrel 810, and further defines the track of accessory plunger 824. The above-described mechanical arrangement results in a reciprocating, thumb-operated, double-plunger syringe device that may be operated with one hand and effects both aspiration and injection.

FIGS. 9A and 9B illustrate another syringe device 900 of a preferred embodiment of the present invention. Syringe device 900 of FIGS. 9A and 9B includes a modified conventional syringe 902 made of plastic, glass, or other suitable material. On syringe 902 there is mounted a needle or cannula 904 having a hub 906. Hypodermic needle or cannula 904 is held on syringe 902 by a conventional needle or cannula fitting 908 such as a luer, Luer-Lok, etc. Syringe 902 includes a syringe barrel 910 with two finger flanges 912 and 914. A syringe plunger 916 inserted into syringe barrel 910 includes a stopper 918, made from rubber or another flexible or tight-sealing material. Mounted on one side of syringe barrel 910 is a gear pulley 920, which is free to rotate. A supplementary plunger 922 having a thumb rest 924 is attached to one side of syringe plunger 916 by a neck piece 926, shown in FIG. 9B, so that supplementary plunger 922 is aligned with gear pulley 920. Functionally, thumb rest 924 of supplementary plunger 922 acts as the thumb rest for syringe plunger 916. Supplementary plunger 922 includes teeth or notches 928 on one side which engage teeth 930 of gear pulley 920. An accessory plunger 932 located outside of syringe barrel 910 includes teeth 934 on one side which engage teeth 930 of gear pulley 920. Accessory plunger 932 also includes a thumb rest 936. A proximal retaining band 938 is fixed to syringe barrel 910 and surrounds plungers 922 and 932 permitting plungers 922 and 932 to move along defined tracks and keeping teeth 928 and 934 of plungers 922 and 932, respectively in contact with gear pulley 920. A distal retaining band 940 is fixed to accessory plunger 932 and surrounds syringe barrel 910 and further defines the track of accessory plunger 932. The above-described mechanical arrangement results in a reciprocating, thumb-operated, double-plunger syringe device that may be operated with one hand and effects both aspiration and injection.

FIGS. 10A and 10B illustrate another syringe device 1000 of a preferred embodiment of the present invention. Syringe device 1000 of FIGS. 10A and 10B includes a modified conventional syringe 1002 made of plastic, glass, or other suitable material. On syringe 1002 there is mounted a needle or cannula 1004 having a hub 1006. Hypodermic needle or cannula 1004 is held on syringe 1002 by a conventional needle or cannula fitting 1008 such as a luer, Luer-Lok, etc. Syringe 1002 includes a syringe barrel 1010 with two finger flanges 1012 and 1014. A syringe plunger 1016 inserted into syringe barrel 1010 includes a stopper 1018, made from rubber or another flexible or tight-sealing material. A U-tube 1020 having arms 1022 and 1024 is mounted on one side of syringe barrel 1010. A supplementary plunger 1026 having a thumb rest 1028 is attached to one side of syringe plunger 1016 by a neck piece 1030, shown in FIG. 10B, so that supplementary plunger 1026 is aligned with U-tube 1020 and so that supplementary plunger 1026 may travel in arm 1022 of U-tube 1020. Functionally, thumb rest 1028 of supplementary plunger 1026 acts as the thumb rest for syringe plunger 1016. An accessory plunger 1032 having a thumb rest 1034 travels in other arm 1024 of U-tube 1020. Supplementary plunger 1026 and accessory plunger 1032 each include an end piece or stopper 1036 and 1038, respectively, which may be made of a flexible material such as rubber. Between two end pieces 1036 and 1038 there is a connector material 1040 which causes one of plungers 1026 or 1028 to move proximally when the other plunger moves distally. In syringe device 1000 shown, connector material 1040 is a hydraulic fluid. However, connector material may also be a spring cable or other stiff, but flexible solid material which extends between the end pieces or is connected at each end to each of the end pieces of the syringe device. The above-described mechanical arrangement results in a reciprocating, thumb-operated, double-plunger syringe device that can be operated with one hand and effects both aspiration and injection.

Figure 11:
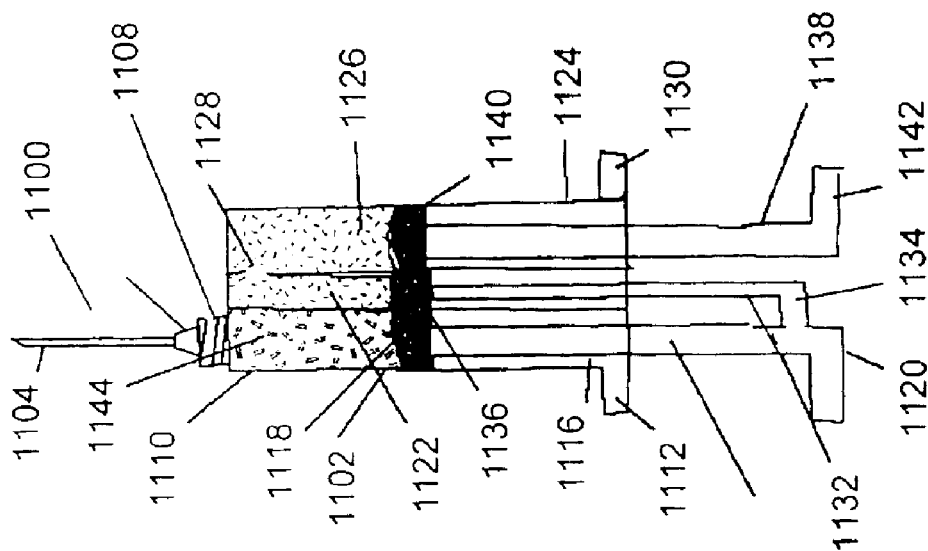

FIG. 11 illustrates another syringe device 1100 of a preferred embodiment of the present invention. Syringe device 1100 of FIG. 11 includes a modified conventional syringe 1102 made of plastic, glass, or other suitable material. On syringe 1102 there is mounted a needle or cannula 1 104 having a hub 1106. Hypodermic needle or cannula 1104 is held on syringe 1102 by a conventional needle or cannula fitting 1108 such as a luer, Luer-Lok, etc. Syringe 1102 includes a syringe barrel 1110 with a finger flange 1112. A syringe plunger 1116 inserted into syringe barrel 1110 and includes a stopper 1118, made from rubber or another flexible or tight-sealing material as well as a thumb rest 1120. Mounted on one side of syringe barrel 1110 are a supplementary hydraulic chamber 1122 and an accessory hydraulic chamber 1124 filled with a hydraulic fluid 1126. Supplementary hydraulic chamber 1122 is in hydraulic communication with accessory hydraulic chamber 1124 by means of an opening 1128. A second finger flange 1130 for syringe device 1100 is mounted on accessory hydraulic chamber 1124 and is effectively mounted on syringe barrel 1110 by means of accessory hydraulic chamber 1124 and supplementary hydraulic chamber 1122. A supplementary plunger 1132 is connected to syringe plunger 1116 by a neck 1134 and extends substantially parallel to syringe plunger 1116. Supplementary plunger 1132 travels within supplementary hydraulic chamber 1122 and includes a stopper 1136 made of a flexible material such as rubber. An accessory plunger 1138 travels within accessory hydraulic chamber 1124 and includes a stopper 1140 made of a flexible material and a thumb rest 1142. Pushing down on supplementary plunger 1116 forces hydraulic fluid 1126 from accessory hydraulic chamber 1122 into supplementary hydraulic chamber 1122, thereby exerting pressure on distal face of supplementary stopper 1138. This in turn forces supplementary stopper 1136 and attached supplementary plunger 1132 upwards so that a medication or other fluid 1140 may be aspirated into syringe barrel 1110. Pushing down on syringe plunger 1116 when supplementary hydraulic 0chamber 1122 is full of hydraulic fluid 1126 forces fluid 1142 out of syringe barrel 1110 and, simultaneously, forces hydraulic fluid 1126 in supplementary hydraulic chamber 1122 into accessory hydraulic chamber 1124. Although the syringe barrel, supplementary hydraulic chamber, and accessory hydraulic chamber are shown as being part of the same housing in the syringe device shown in FIG. 11, they may also be formed as separate units and attached together. The above-described mechanical arrangement results in a reciprocating, thumb-operated, double-plunger syringe device that may be operated with one hand and effects both aspiration and injection.

Figure 12:
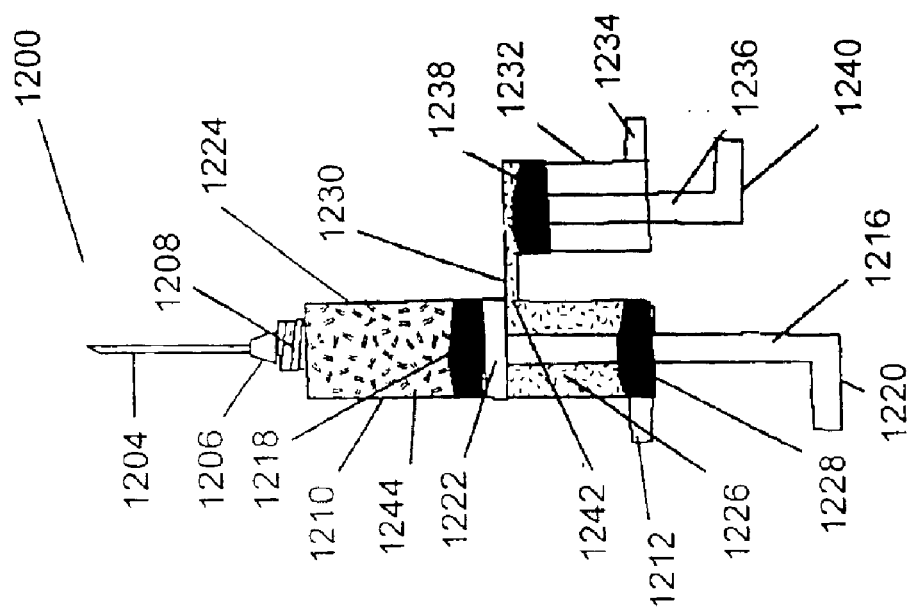

FIG. 12 illustrates another syringe device 1200 of a preferred embodiment of the present invention. Syringe device 1200 of FIG. 12 includes a modified conventional syringe 1202 made of plastic, glass, or other suitable material. On syringe 1202 there is mounted a needle or cannula 1204 having a hub 1206. Hypodermic needle or cannula 1204 is held on syringe 1202 by a conventional needle or cannula fitting 1208 such as a luer, Luer-Lok, etc. Syringe 1202 includes a syringe barrel 1210 with a finger flange 1212. A syringe plunger 1216 inserted into syringe barrel 1210 includes a lower stopper 1218, made from rubber or another flexible or tight-sealing material, and a thumb rest 1220. Mounted in syringe barrel 1210 is a barrel divider 1222 which divides syringe barrel 1210 into a lower chamber 1224 and an upper chamber 1226. Syringe plunger 1216 extends through an opening (not shown) in barrel divider 1222 and lower stopper 1218 abuts against a bottom surface of the barrel divider 1222 when syringe plunger 1216 is fully retracted, as shown in FIG. 12. An upper stopper 1228 is also mounted on syringe plunger 1216 and slides within and acts as a movable upper seal for upper chamber 1226. Upper stopper 1228 is preferably made of a flexible material similar to that of lower stopper 1218. Upper chamber 1226 is connected by a passageway 1230 to an accessory hydraulic chamber 1232. A second finger flange 1234 for syringe device 1200 is mounted on accessory hydraulic chamber 1232 and is effectively mounted on syringe barrel 1210 by means of accessory hydraulic chamber 1232. An accessory plunger 1236 travels within accessory hydraulic chamber 1230 and includes a stopper 1238 made of a flexible material and a thumb rest 1240. A hydraulic fluid 1240 fills upper chamber 1228, passageway 1230, and accessory hydraulic chamber 1232. Pushing down on accessory plunger 1236 forces hydraulic fluid 1240 from accessory hydraulic chamber 1232 into upper chamber 1224, thereby exerting pressure on a distal surface 1242 of upper stopper 1228. This in turn forces stopper 1228 and attached syringe plunger 1216 upwards so that a fluid or medication 1242 may be aspirated into lower chamber 1224. Pushing down on syringe plunger 1216 when upper chamber 1226 is full of hydraulic fluid 1240 as shown in FIG. 12 forces fluid 1242 out of lower chamber 1224 and, simultaneously, forces hydraulic fluid 1240 in upper chamber 1236 and into accessory hydraulic chamber 1232. The above-described mechanical arrangement results in a reciprocating, thumb-operated, double-plunger syringe device that may be operated with one hand and effects both aspiration and injection.

Although the accessory chamber and syringe barrel are shown as being separated in the syringe device of FIG. 12, the accessory chamber may also be mounted directly on the syringe barrel.

FIG. 13 illustrates another syringe device 1300 of a preferred embodiment of the present invention. Syringe device 1300 of FIG. 13 includes a modified conventional first syringe 1302 made of plastic, glass, or other suitable material. On first syringe 1302 there is mounted a first needle or cannula 1304 having a first hub 1306. Hypodermic first needle or cannula 1304 is held on first syringe 1302 by a conventional first needle or cannula fitting 1308 such as a luer, Luer-Lok, etc. First syringe 1302 includes a first syringe barrel 1310 with a first finger flange 1312. A first syringe plunger 1314 inserted into first syringe barrel 1310 includes a first stopper 1316, made from rubber or another flexible or tight-sealing material, and a thumb rest 1316. First syringe stopper 1316 divides syringe barrel 1310 into a first lower chamber 1320 and a first upper chamber 1322 which each changing in size as first syringe plunger 1314 moves within syringe barrel 1310. A fluid tight seal 1324 seals a top of first upper chamber 1322 and includes an opening (not shown) through which first syringe plunger 1314 extends. Mounted on a side of first syringe 1302 is a second syringe 1332. On second syringe 1332 there is mounted a second needle or cannula 1334 having a second hub 1336. Second hypodermic needle or cannula 1334 is held on second syringe 1332 by a conventional second needle or cannula fitting 1338 such as a luer, Luer-Lok, etc. Second syringe 1332 includes a second syringe barrel 1340 with a second finger flange 1342. A second syringe plunger 1344 inserted into second syringe barrel 1340 includes a second stopper 1346, made from rubber or another flexible or tight-sealing material, and a thumb rest 1348. Second syringe stopper 1342 divides second syringe barrel 1330 into a second lower chamber 1350 and a second upper chamber 1352 which each change in size as second syringe plunger 1336 moves within second syringe barrel 1330. At a top of second upper chamber 1352 is a fluid tight seal 1354 which seals the top of second upper chamber 1352 and includes an opening (not shown) through which second syringe plunger 1336 extends. First upper chamber 1322 and second upper chamber 1352 are in fluid communication by means of an opening 1356 between chambers 1322 and 1352. Chambers 1322 and 1352 are filled with a hydraulic fluid 1358. Pulling up on first plunger 1314 aspirates a first medication or fluid 1360 into first lower chamber 1320 and, simultaneously, forces hydraulic fluid 1358 from first upper chamber 1322 into second upper chamber 1352. Thus, pressure is exerted on a proximal surface 1362 of second stopper 1346, forcing second stopper 1346 and attached second syringe plunger 1344 downwards so that a second medication or fluid 1364 is forced from second lower chamber 1350. Pulling up on second plunger 1336 aspirates additional second fluid 1364 into second lower chamber 1350 and, simultaneously, forces hydraulic fluid 1358 from second upper chamber 1352 into first upper chamber 1322. Thus, pressure is exerted on a proximal surface 1366 of first stopper 1316, forcing first stopper 1316 and attached first syringe plunger 1314 downwards so that the medication or fluid 1360 is forced from first lower chamber 1320. The above-described mechanical arrangement results in a reciprocating, thumb-operated, double-plunger syringe device that may be operated with one hand and effects both aspiration and injection.

Although the syringe device of FIG. 13 includes two syringes, one or the other of the two syringes may act as an accessory barrel and have a lower chamber which only contains air. In this situation, it may be desirable to provide a larger opening in the lower chamber of the accessory barrel so that the air in the lower chamber is free to escape.

Figure 15A:
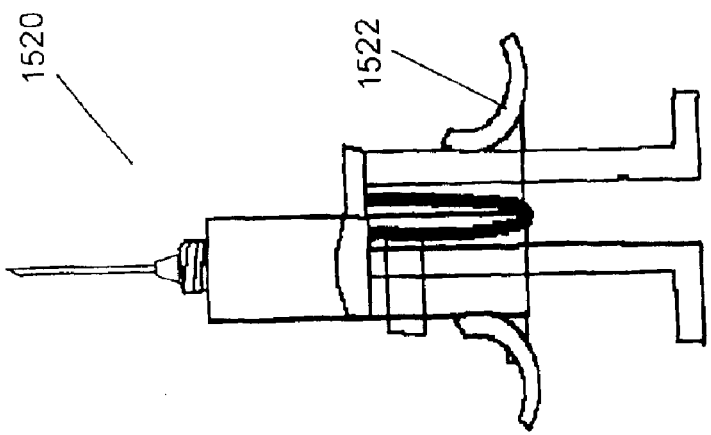
Figure 15B:
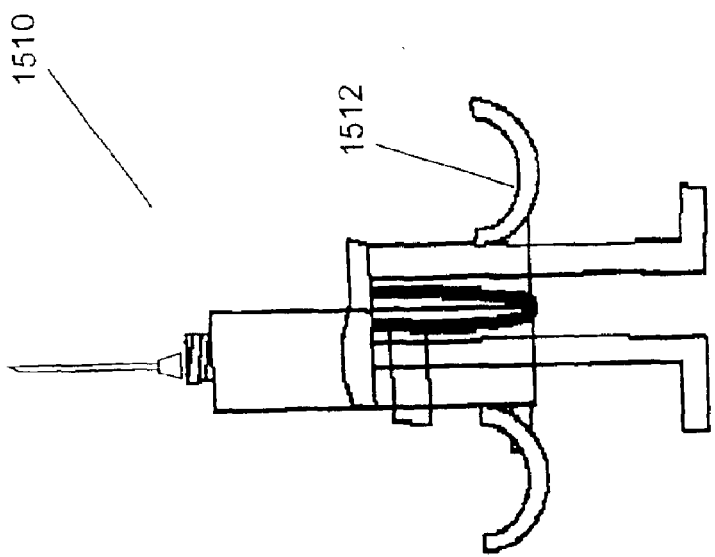
Figure 15C:
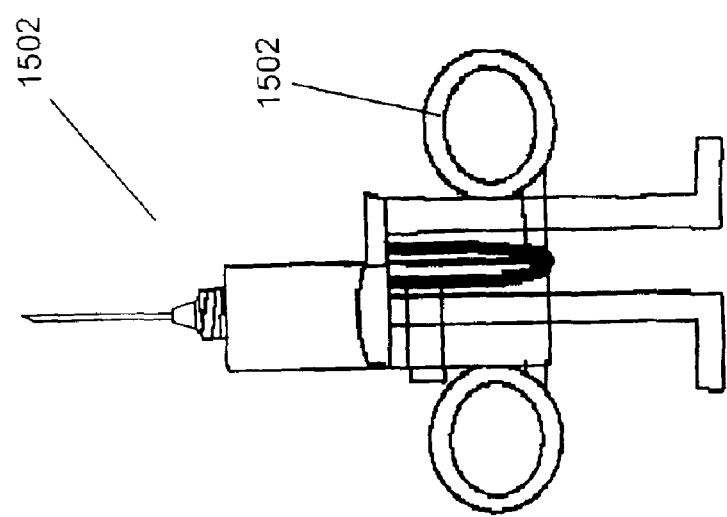

The presence of two plungers in the syringe device of the present invention and the resulting movement of a user's thumb between the two plungers may result in temporary instability of the syringe. One option to minimize this is the use of a handle as shown in FIGS. 14A and 14B. FIGS. 14A and 14B illustrates another syringe device 1400 of the present invention having a syringe 1402 and accessory chamber 1404 on which are mounted a gun-like handle 1406 and finger ring 1408 for a user's index finger that allow syringe device 1402 to be gripped more securely. Although finger flanges are shown in the syringe device shown in FIGS. 14A and 14B, it is not necessary to include such finger flanges in this embodiment, the finger ring functions similar to the finger flanges in the previously described embodiments of the present invention. Another option is the development of finger flanges with greater stability as shown in FIGS. 15A, 15B, and 15C. The most simple technique for stability is to exaggerate the size and surface area of the finger flange. FIGS. 15A, 15B, and 15C illustrate various types of finger flanges which may be used with syringe devices of the present invention. FIG. 15A illustrates a syringe device 1500 having circular finger flanges 1502 FIG. 15B illustrates a syringe device 1510 having half-ring finger flanges 1512. FIG. 15C illustrates a syringe device 1520 having curvilinear flanges 1522.

FIGS. 16A, 16B, 16C, and 16D illustrate the use of another syringe device 1600 of the present invention. Syringe device 1600 includes a Syringe 1602 having two finger flanges 1604 and 1606, a syringe plunger 1608, a thumb rest 1610, a reciprocating plunger 1612, a thumb rest 1614, a guide piece 1616, an opening 1618 in finger flange 1606 through which reciprocating plunger 1612 extends, and a track 1620 on a side of syringe 1602 along which guide piece 1616 and attached reciprocating plunger 1612 moves. To aspirate, a user's fingers are placed on finger flanges 1604 and 1606 and the user's thumb is placed on thumb rest 1614 of reciprocating plunger 1612 as shown in FIG. 16A. Thumb rest 1614 of reciprocating plunger 1612 is then squeezed between the fingers and thumb resulting in an effective aspiration and the generation of a powerful vacuum as shown in FIG. 16B. The power result from use of forceful flexion of not only intrinsic muscles of the hand, but also powerful flexors of the forearm. Since the motion is smooth and in one direction, there is no rotation, twist, or other loss of control, resulting in a smooth aspiration with excellent control. For aspiration procedures in which a syringe must be held still during the procedure, the syringe of the present invention has special advantages as the barrel of the syringe does not advance beyond the plane of the digits of the hand. Thus, creating an extremely stable platform. Injection with the syringe of the present invention is identical to that of a standard syringe, using powerful flexor muscles of the hand and forearm. Injection with this aspiration syringe may be easily accomplished with one hand, freeing up the other hand for other necessary tasks or procedures. In this technique, the 2nd (index) and 3rd fingers (middle finger) remain on finger flange 1604 of syringe 1602 and the thumb is moved laterally from thumb rest 1614 of reciprocating plunger 1612 to thumb rest 1610 of syringe plunger 1608, as shown in FIG. 16C. Flange 1604 and thumb rest 1614 are brought together due to contraction of the powerful flexor muscles of the hand and forearm resulting in an effective injection with all the power of a conventional syringe as shown in FIG. 16D.

Any of the above-described reciprocating syringes of the present invention may be used as a pump by the addition of an external or integrated valve system consisting of two one-way valves as shown in FIGS. 17A and 17B. FIG. 17A shows a syringe device 1700 of the present invention having a double one-way valve 1702 attached. Arrows 1704 show the direction of flow through the valve. FIG. 17B shows a syringe device 1710 of the present invention having two, one-way valves 1712 and 1714 mounted on a syringe barrel 1716. Value 1714 is mounted over and in communication with an opening 1718 at a distal end of syringe barrel 1716. Valve 1714 is mounted over and in communication with an opening 1720 in a side wall 1724 of syringe barrel 1716. Arrows 1724 show direction of flow. The direction of the one-way valves determines whether the syringe functions as an infusion or aspiration pump. An integrated valve system transforms the syringe into a dedicated pump. The valves themselves may be dedicated uni-directional, or may be adjustable: on-bi-directional, on-aspiration, on-infusion, or off, creating greater flexibility of the syringe pump device. These devices may also be used as a vacuum or pressure device for procedures, particularly if a distal pressure or vacuum chamber is added and the syringe is then used as a topping device.

Any of the previously described reciprocating devices: line driven, line-driven-pulley post, gear-driven, U-tube-driven, or hydraulic-driven, etc. may be used to drive a reciprocating, thumb-operated, double plunger syringe of the present invention having double functional barrels. Examples of double functional barrels are shown in FIGS. 18A and 18B, although the double functional barrel designs of the present invention also encompass using the reciprocating devices discussed previously for the single barrel designs of the present invention.

FIG. 18A shows a double functional barrel syringe device 1800 having a line drive reciprocating device and FIG. 18B shows a double functional barrel syringe device 1810 having a pulley post line drive reciprocating device. The double functional barrel syringe devices of the present invention may be used identically to the single functional barrel versions of the reciprocating syringes, both as an aspiration-injection syringe or as a pump. However, with two functional barrels, this design has special applications and efficiency as a pump. This results from the fact that the double functional barrel design permits twice the amount of volume to be transferred with a complete stroke cycle compared to the single functional barrel designs.

To function as a pump, the barrels may be fitted with unidirectional valves. The direction of the one-way valves determines whether the syringe functions as an infusion, aspiration, or irrigation pump. When the direction of the valve systems are opposite in the two barrels, an irrigation pump is created. FIG. 18C shows a syringe device 1820 of the present invention having two double one-way valves 1822 and 1824 mounted on syringe device 1820. Valves 1822 and 1824 operate in opposite directions shown by arrows 1826, causing the syringe device 1820 to function as an irrigation pump. FIG. 18D shows a syringe device 1830 comprising two syringes 1832 and 1834. Syringe 1832 has a one-way valve 1836 mounted over and communication with an opening 1838 at a distal end of syringe 1832 and a one-way valve 1840 mounted over and communication with an opening 1842 in a wall of syringe 1832. Syringe 1834, which is mounted on syringe 1832, has a one-way valve 1844 mounted over and in communication with an opening 1846 at a distal end of syringe 1834 and a one-way valve 1848 mounted over and in communication with an opening 1850 in a wall of syringe 1834. Valves 1836 and 1840 of syringe 1832 operate in opposite direction to valves 1844 and 1840 of syringe 1834, as shown by arrows 1852, causing syringe device 1830 to function as a dedicated irrigation pump.

When the direction of the valve systems are in the same direction, either an aspiration or infusion pump is created, depending on the direction of the valves. An integrated valve system transforms the syringe into a dedicated pump. The valves themselves may be dedicated uni-directional, or may be adjustable: on-bi-directional, on-aspiration, on-infusion, or off, creating greater flexibility of the individual syringe pump device.

FIG. 18E shows a syringe device 1860 of the present invention having two one-way valves 1862 and 1864 in which valves 1862, 1864 operate in the same directions as shown by arrows 1866. This causes syringe device 1860 to function as an aspiration pump. FIG. 18F shows a syringe device 1870 comprising two syringes 1872 and 1874. Syringe 1872 has a one-way valve 1876 mounted over and in communication with an opening 1878 at a distal end of syringe 1862 and a one-way valve 1880 mounted over and in communication with an opening 1882 in a wall of syringe 1872. Syringe 1874, which is mounted on syringe 1872, has a one-way valve 1884 mounted over and in communication with an opening 1886 at a distal end of syringe 1874 and a one-way valve 1888 mounted over and in communication with an opening 1890 in a wall of syringe 1874. Valves 1876 and 1880 of syringe 1872 operate in the same direction as valves 1884 and 1888 of syringe 1874, as shown by arrows 1892, thus, causing syringe device 1860 to function as a dedicated aspiration pump. These devices may also be used as a vacuum or pressure device for procedures, particularly if a distal pressure or vacuum chamber is added and the syringe is then used as a topping device.

The reciprocating syringe device of the present invention has the following advantages over conventional syringes: 1) single-handed aspiration may be accomplished easily; 2) injection is performed identically to aspiration with only a change in the thumb position while the index and middle fingers do not change position; 3) the other hand is freed and may be used for other tasks; 4) the power of the aspiration is maximized by the use of hand and forearm flexors rather than weak extensors of the thumb; 5) exquisite control of the syringe is maintained because it is gripped by fingers and not the palm; 6) there is no rotational twist during forceful movement of the plunger resulting in markedly improved performance over other single-handed aspiration techniques; 7) the same hand grip position may be used throughout the aspiration/injection cycles unlike other single-hand techniques; 8) for procedures that require constant aspiration with one hand, this syringe is ideal because it may be held in an aspiration position with or without a locking device; 9) both single functional barrel and double functional barrel versions may be converted into single-hand-held pumps by the addition of unidirectional valves; and 10) reciprocating, thumb-operated, double-plunger syringe for single-handed use of all sizes: 1, 3, 5, 10, 20, 60 cc; may be constructed with the same effectiveness. For the above reasons, syringes of the present invention are clearly superior to other single-handed devices currently in use.

Although the above-described embodiments of the present invention are manually operated, syringes of the present invention may also be mechanically, motor, electrically, or computer-driven or controlled devices. For example, in a syringe device of the present invention having two barrels and one or more valves associated with each barrel, the reciprocal motion of the plungers for each of the barrels may be controlled with a crankshaft-like device which pushes one plunger down as it pulls the other plunger up. Such a crankshaft-like device may be powered in a variety of ways and such a crankshaft device may be used to operate all of the plungers in syringe device of the present invention having multiple barrels. In embodiments of the present invention which are not manually operated, finger flanges shown in the above-described manually operated embodiments may be eliminated and syringe barrel, barrels, guide tracks, etc,. may be held in place relative to the plunger, plungers, reciprocating members, etc., by other means, such as mounting the syringe barrel in place.

Although in the above-described embodiments of the syringe device have been primarily described as being used as a medical device, this device may also be used in other applications such as industrial applications, automotive applications, etc.

Finally, the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed:

1. A syringe device comprising:
    a first syringe comprising:
    a first syringe barrel including an opening at a distal end thereof through which fluid may be forced or aspirated; and
    a first syringe plunger sliding within said first syringe barrel for forcing fluid through said first syringe barrel opening, said first syringe plunger including a stopper at a distal end thereof which sealingly and slidably engages said first barrel;
    a reciprocating member which moves along a track parallel to the axial direction of said first syringe; and
    a reciprocating device connecting said first syringe plunger to said reciprocating member so that when one member of the group consisting of said first syringe plunger and said reciprocating member moves proximally, the other member of said group is forced to move distally, wherein said first syringe plunger includes teeth on one side thereof, said reciprocating member comprises a plunger having teeth on one side thereof, and said reciprocating device comprises: a pulley post mounted on and extending axially from said first syringe barrel; a gear pulley rotatably mounted on said pulley post and having teeth for engaging said teeth on said first syringe plunger and said reciprocating member; a first retaining band fixed to said first syringe barrel and surrounding said first syringe plunger and said reciprocating member; and a second retaining band fixed to said reciprocating member and surrounding first syringe barrel; wherein, said syringe plunger includes a thumb rest at a proximal end thereof for allowing a user to push said first syringe plunger distally; wherein said reciprocating member includes a second thumb rest at a proximal end thereof for allowing the user to push said reciprocating member distally; and wherein said first syringe barrel includes first and second finger flanges for gripping by a user, said first and second finger flanges mounted on and extending laterally from a proximal end of said first syringe barrel.

2. A syringe device comprising:

a first syringe comprising:

a first syringe barrel including an opening at a distal end thereof through which fluid may be forced or aspirated; and a first syringe plunger sliding within said first syringe barrel for forcing fluid through said first syringe barrel opening, said first syringe plunger including a stopper at a distal end thereof which sealingly and slidably engages said first syringe barrel;

a reciprocating member which moves along a track parallel to the axial direction of said first syringe; and a reciprocating device connecting said first syringe plunger to said reciprocating member so that when one member of the group consisting of said first syringe plunger and said reciprocating member moves proximally, the other member of said group is forced to move distally, wherein said first syringe plunger includes teeth on one side thereof, said reciprocating member comprises a plunger having teeth on one side thereof, and said reciprocating device comprises: a pulley post mounted on and extending axially from said first syringe barrel; a gear pulley rotatably mounted on said pulley post and having teeth for engaging said teeth on said first syringe plunger and said reciprocating member; a first retaining band fixed to said pulley post and surrounding said first syringe plunger and said reciprocating member; and a second retaining band fixed to said reciprocating member and surrounding first syringe barrel, wherein, said first syringe plunger includes a thumb rest at a proximal end thereof for allowing a user to push said first syringe plunger distally; wherein said reciprocating member includes a second thumb rest at a proximal end thereof for allowing the user to push said reciprocating member distally; and wherein said first syringe barrel includes first and second finger flanges for gripping by a user, said first and second finger flanges mounted on and extending laterally from a proximal end of said first syringe barrel.

3. A syringe device comprising:

a first syringe comprising:

a first syringe barrel including an opening at a distal end thereof through which fluid may be forced or aspirated; and a first syringe plunger sliding within said first syringe barrel for forcing fluid through said first syringe barrel opening, said first syringe plunger including a stopper at a distal end thereof which sealingly and slidably engages said first syringe barrel;

a reciprocating member which moves along a track parallel to the axial direction of said first syringe; and a reciprocating device connecting said first syringe plunger to said reciprocating member so that when one member of the group consisting of said first syringe plunger and said reciprocating member moves proximally, the other member of said group is forced to move distally, wherein said first syringe plunger includes a supplementary plunger connected to said first syringe plunger and extending in a direction parallel to said first syringe plunger, said supplementary plunger having teeth on one side thereof; said reciprocating member comprises a plunger having teeth on one side thereof; and said reciprocating device comprises a gear pulley rotatably mounted on said first syringe plunger and having teeth for engaging said teeth on said supplementary plunger and said reciprocating member, a first retaining band fixed to said first syringe barrel and surrounding said first syringe plunger and said reciprocating member, and a second retaining band fixed to said reciprocating member and surrounding said first syringe barrel; wherein, said first syringe plunger includes a thumb rest at a proximal end thereof for allowing a user to push said first syringe plunger distally; wherein said reciprocating member includes a second thumb rest at a proximal end thereof for allowing the user to push said reciprocating member distally; and wherein said first syringe barrel includes first and second finger flanges for gripping by a user, said first and second finger flanges mounted on and extending laterally from a proximal end of said first syringe barrel.

4. A syringe device comprising:

a first syringe comprising:

a first syringe barrel including an opening at a distal end thereof through which fluid may be forced or aspirated and including first and second finger flanges for gripping by a user, said first and second finger flanges being mounted on and extending laterally from a proximal end of said first syringe barrel; and a first syringe plunger sliding within said first syringe barrel for forcing fluid through said first syringe barrel opening, said first syringe plunger including a stopper at a distal end thereof which sealingly and slidably engages said first syringe barrel and including a first thumb rest at a proximal end thereof for allowing a user to pull said first syringe plunger proximally, said first syringe plunger including a supplementary plunger connected to said first syringe plunger and extending in a direction parallel to said first syringe plunger;

a reciprocating member which moves along a track parallel to the axial direction of said first syringe, said reciprocating member including a second thumb rest at a proximal end thereof for allowing the user to pull said reciprocating member proximally; and a reciprocating device connecting said first syringe plunger to said reciprocating member so that when either one of the members of the group consisting of said first syringe plunger and said reciprocating member moves proximally, the other member of said group is forced to move distally, wherein said syringe device may be held and operated by one hand, said reciprocating device comprising: a U-tube mounted on at least one side of said first syringe barrel, said U-tube having two arms into which each of said supplementary plunger, and said reciprocating member extends, respectively; and a connecter material extending between distal ends of said supplementary plunger and said reciprocating member within said U-tube.

5. The syringe device of claim 4, wherein said connector material comprises a hydraulic fluid, and each of said supplementary plunger and said reciprocating member includes a stopper means which sealingly and slidably engages each of said respective chambers for exerting pressure on said hydraulic fluid and for receiving pressure from said hydraulic fluid.

6. The syringe device of claim 4, wherein said connector material comprises a flexible solid material.

7. The syringe device of claim 6, wherein said flexible solid material is joined at each end to said supplementary plunger and said reciprocating member respectively.

8. A syringe device comprising:

a first syringe comprising:

a first syringe barrel including an opening at a distal end thereof through which fluid may be forced or aspirated and including first and second finger flanges for gripping by a user, said first and second finger flanges being mounted on and extending laterally from a proximal end of said first syringe barrel; and a first syringe plunger sliding within said first syringe barrel for forcing fluid through said first syringe barrel opening, said first syringe plunger including a stopper at a distal end thereof which sealingly and slidably engages said first syringe barrel and including a first thumb rest at a proximal end thereof for allowing a user to pull said first syringe plunger proximally;

a reciprocating member which moves alone a track parallel to the axial direction of said first syringe, said reciprocating member including a second thumb rest at a proximal end thereof for allowing the user to pull said reciprocating member proximally; and a reciprocating device connecting said first syringe plunger to said reciprocating member so that when either one of the members of the group consisting of said first syringe plunger and said reciprocating member moves proximally, the other member of said group is forced to move distally, wherein said syringe device may be held and operated by one hand, said reciprocating device comprising two hydraulic chambers mounted on said first syringe barrel filled with a hydraulic fluid and in hydraulic communication with each other, wherein said first syringe plunger includes a supplementary plunger connected to said first syringe plunger and extending in a direction parallel to said first syringe plunger; and wherein said supplementary plunger travels in one of said two hydraulic chambers and said reciprocating member travels within the other of said two hydraulic chambers.

9. A syringe device comprising:

a first syringe comprising:

a first syringe barrel including an opening at a distal end thereof through which fluid may be forced or aspirated and including first and second finger flanges for gripping by a user, said first and second finger flanges being mounted on and extending laterally from a proximal end of said first syringe barrel; and a first syringe plunger sliding within said first syringe barrel for forcing fluid through said first syringe barrel opening, said first syringe plunger including a stopper at a distal end thereof which sealingly and slidably engages said first syringe barrel and including a first thumb rest at a proximal end thereof for allowing a user to pull said first syringe plunger proximally, said first syringe plunger including a barrel divider mounted in said first syringe barrel which divides said first syringe barrel into a lower and an upper chamber;

a reciprocating member which moves along a track parallel to the axial direction of said first syringe, said reciprocating member including a second thumb rest at a proximal end thereof for allowing the user to pull said reciprocating member proximally; and a reciprocating device connecting said first syringe plunger to said reciprocating member so that when either one of the members of the group consisting of said first syringe plunger and said reciprocating member moves proximally, the other member of said group is forced to move distally, wherein said syringe device may be held and operated by one hand, said reciprocating device comprising: an accessory chamber in which said reciprocating member travels, which is mounted on said first syringe barrel and which is in fluid communication with said upper chamber; and a hydraulic fluid filling said upper chamber and said accessory chamber; wherein said first syringe plunger includes an upper stopper means for exerting pressure on and receiving pressure from said hydraulic fluid which is mounted on said first syringe plunger and which travels within said upper chamber and sealingly and slidably engages said upper chamber; and wherein said reciprocating member includes an accessory stopper means chamber for exerting pressure on and receiving pressure from said hydraulic fluid which is mounted on said reciprocating member and which travels within said accessory chamber and sealingly and slidably engages said accessory chamber.

10. A syringe device comprising:

a first syringe comprising:

a first syringe barrel including an opening at a distal end thereof through which fluid may be forced or aspirated and including first and second finger flanges for gripping by a user, said first and second finger flanges being mounted on and extending laterally from a proximal end of said first syringe barrel; and a first syringe plunger sliding within said first syringe barrel for forcing fluid through said first syringe barrel opening, said first syringe plunger including a stopper at a distal end thereof which sealingly and slidably engages said first syringe barrel and including a first thumb rest at a proximal end thereof for allowing a user to pull said first syringe plunger proximally, said first syringe plunger stopper dividing said first syringe barrel into a lower and an upper barrel chamber, said upper barrel chamber including a barrel proximal seal through which said first syringe plunger extends and which seals a proximal end of said upper chamber;

a reciprocating member which moves along a track parallel to the axial direction of said first syringe, said reciprocating member including a second thumb rest at a proximal end thereof for allowing the user to pull said reciprocating member proximally, said reciprocating member including an accessory stopper sealingly and slidably engaging an accessory chamber in which said reciprocating member travels, said accessory stopper dividing said accessory chamber into a lower and upper accessory chamber, said accessory upper chamber including an accessory chamber proximal seal through which said reciprocating member extends and which seals a proximal end of said accessory chamber; and a reciprocating device connecting said first syringe plunger to said reciprocating member so that when either one of the members of the group consisting of said first syringe plunger and said reciprocating member moves proximally, the other member of said group is forced to move distally, wherein said syringe device may be held and operated by one hand, said reciprocating device comprising: said upper barrel chamber and said upper accessory chamber which are in hydraulic communication with each other and a hydraulic fluid which fill said upper barrel chamber and said upper accessory chamber, an accessory chamber in which said reciprocating member travels and which is mounted on said first syringe barrel and which is fluid communication with said upper chamber; and a hydraulic fluid filling said upper chamber and said accessory chamber; and wherein said first syringe plunger stopper and said accessory stopper each include a respective upper surface for exerting pressure on and receiving pressure from said hydraulic fluid.

11. The syringe device of claim 10, wherein said accessory chamber comprises an accessory first syringe barrel including an opening at a distal end of said accessory barrel through which fluid from said first syringe barrel may be forced or aspirated.

12. A syringe device comprising:

a first syringe comprising:

a first syringe barrel including a first opening at a distal end thereof through which fluid may be forced or aspirated and including first and second finger flanges for gripping by a user, said first and second finger flanges being mounted on and extending laterally from a proximal end of said first syringe barrel; and a first syringe plunger sliding within said first syringe barrel for forcing fluid through said first syringe barrel opening, said first syringe plunger including a stopper at a distal end thereof which sealingly and slidably engages said first syringe barrel and including a first thumb rest at a proximal end thereof for allowing a user to push said syringe plunger distally;

a reciprocating member which moves along a track parallel to the axial direction of said first syringe, said reciprocating member including a second thumb rest at a proximal end thereof for allowing the user to push said reciprocating member distally; and a reciprocating device connecting said first syringe plunger to said reciprocating member so that when one member of the group consisting of said first syringe plunger and said reciprocating member moves distally, the other member of said group is forced to move proximally, wherein said first syringe plunger includes teeth on one side thereof, said reciprocating member comprises a plunger having teeth on one side thereof, and said reciprocating device comprises: a pulley post mounted on and extending axially from said first syringe barrel; a gear pulley rotatably mounted on said pulley post and having teeth for engaging said teeth on said first syringe plunger and said reciprocating member; a first retaining band fixed to said first syringe barrel and surrounding said first syringe plunger and said reciprocating member; and a second retaining band fixed to said reciprocating member and surrounding first syringe barrel.

13. A syringe device comprising:

a first syringe comprising:

a first syringe barrel including a first opening at a distal end thereof through which fluid may be forced or aspirated and including first and second finger flanges for gripping by a user, said first and second finger flanges being mounted on and extending laterally from a proximal end of said first syringe barrel; and a first syringe plunger sliding within said first syringe barrel for forcing fluid through said first syringe barrel opening, said first syringe plunger including a stopper at a distal end thereof which sealingly and slidably engages said first syringe barrel and including a first thumb rest at a proximal end thereof for allowing a user to push said syringe plunger distally;

a reciprocating member which moves along a track parallel to the axial direction of said first syringe, said reciprocating member including a second thumb rest at a proximal end thereof for allowing the user to push said reciprocating member distally; and a reciprocating device connecting said first syringe plunger to said reciprocating member so that when one member of the group consisting of said first syringe plunger and said reciprocating member moves distally, the other member of said group is forced to move proximally, wherein said first syringe plunger includes teeth on one side thereof, said reciprocating member comprises a plunger having teeth on one side thereof, and said reciprocating device comprises: a pulley post mounted on and extending axially from said first syringe barrel; a gear pulley rotatably mounted on said pulley post and having teeth for engaging said teeth on said first syringe plunger and said reciprocating member; a first retaining band fixed to said pulley post and surrounding said first syringe plunger and said reciprocating member; and a second retaining band fixed to said reciprocating member and surrounding first syringe barrel.

14. A syringe device comprising:

a first syringe comprising:

a first syringe barrel including a first opening at a distal end thereof through which fluid may be forced or aspirated and including first and second finger flanges for gripping by a user, said first and second finger flanges being mounted on and extending laterally from a proximal end of said first syringe barrel; and a first syringe plunger sliding within said first syringe barrel for forcing fluid through said first syringe barrel opening, said first syringe plunger including a stopper at a distal end thereof which sealingly and slidably engages said first syringe barrel and including a first thumb rest at a proximal end thereof for allowing a user to push said syringe plunger distally;

a reciprocating member which moves along a track parallel to the axial direction of said first syringe, said reciprocating member including a second thumb rest at a proximal end thereof for allowing the user to push said reciprocating member distally; and a reciprocating device connecting said first syringe plunger to said reciprocating member so that when one member of the group consisting of said first syringe plunger and said reciprocating member moves distally, the other member of said group is forced to move proximally, wherein said first syringe plunger includes a supplementary plunger connected to said first syringe plunger and extending in a direction parallel to said first syringe plunger, said supplementary plunger having teeth on one side thereof; said reciprocating member comprises a plunger having teeth on one side thereof; and said reciprocating device comprises a gear pulley rotatably mounted on said first syringe plunger and having teeth for engaging said teeth on said supplementary plunger and said reciprocating member, a first retaining band fixed to said first syringe barrel and surrounding said first syringe plunger and said reciprocating member, and a second retaining band fixed to said reciprocating member and surrounding said first syringe barrel.

* * * * *